United States Patent [19]
Charpenet et al.

[11] Patent Number: 5,976,148
[45] Date of Patent: Nov. 2, 1999

[54] SET OF ANCILLARY EQUIPMENT FOR THE IMPLANTATION OF ACETABULAR CUPS OF HIP PROSTHESIS, AND PROSTHETIC ACETABULAR CUP ASSEMBLY READY TO BE IMPLANTED

[75] Inventors: Remy Charpenet, Epinal; Marc Paulin, Chaumont; Jacques Preaut, Bar Le Duc, all of France

[73] Assignee: PPC, Bar le Duc, France

[21] Appl. No.: 08/968,436

[22] Filed: Nov. 12, 1997

[30] Foreign Application Priority Data

Nov. 12, 1996 [FR] France .................................... 96 13761

[51] Int. Cl.⁶ .............................. A61B 17/92; A61F 2/34
[52] U.S. Cl. ................................ 606/91; 606/81; 606/99; 606/100; 623/22
[58] Field of Search ................................ 606/91, 81, 80, 606/79, 89, 86, 99, 100; 623/22, 25

[56] References Cited

U.S. PATENT DOCUMENTS

| | | |
|---|---|---|
| 4,716,894 | 1/1988 | Lazzeri et al. |
| 5,116,339 | 5/1992 | Glock ......................................... 606/91 |
| 5,364,403 | 11/1994 | Peterson et al. ........................... 606/91 |
| 5,540,697 | 7/1996 | Rehmann et al. ......................... 606/91 |

FOREIGN PATENT DOCUMENTS

| | | |
|---|---|---|
| 0 456 580 | 11/1991 | European Pat. Off. . |
| 0 687 452 | 12/1995 | European Pat. Off. . |
| 0 696 439 | 2/1996 | European Pat. Off. . |
| 2 682 286 | 4/1993 | France . |
| 2 696 341 | 4/1994 | France . |
| 2 710 522 | 4/1995 | France . |
| 2 299 758 | 10/1996 | United Kingdom . |
| WO 82/02145 | 7/1982 | WIPO . |
| WO 86/05384 | 9/1986 | WIPO . |
| WO 92/18067 | 10/1992 | WIPO . |

*Primary Examiner*—Michael Buiz
*Assistant Examiner*—David O. Reip
*Attorney, Agent, or Firm*—Young & Thompson

[57] ABSTRACT

Set of ancillary equipment for the implantation of acetabular cups (1) of hip prostheses, of the type having a substantially hemispherical corolla, consisting of expandable petals (2) which are provided with external barbs (5). The set comprises an obturator (7) for closing the petals, under elastic radial stress, in a position in which they are drawn together, elements (8, 9) for holding this obturator on the edges of the petals by connection with the bottom of the acetabular cup, an ancillary impaction device with which it is possible to impact the acetabular cup, freeing its petals by extraction of the obturator. The set also comprises a plate which expands the petals and which can be introduced into these petals after extraction of the obturator and release of the petals, and an ancillary device with which it is possible to drive the plate into the acetabular cup in order to bring about the radial expansion of the petals after impaction, so as to ensure the anchoring of the acetabular cup by penetration of the anchoring barbs into the osseous wall of the acetabulum.

10 Claims, 5 Drawing Sheets

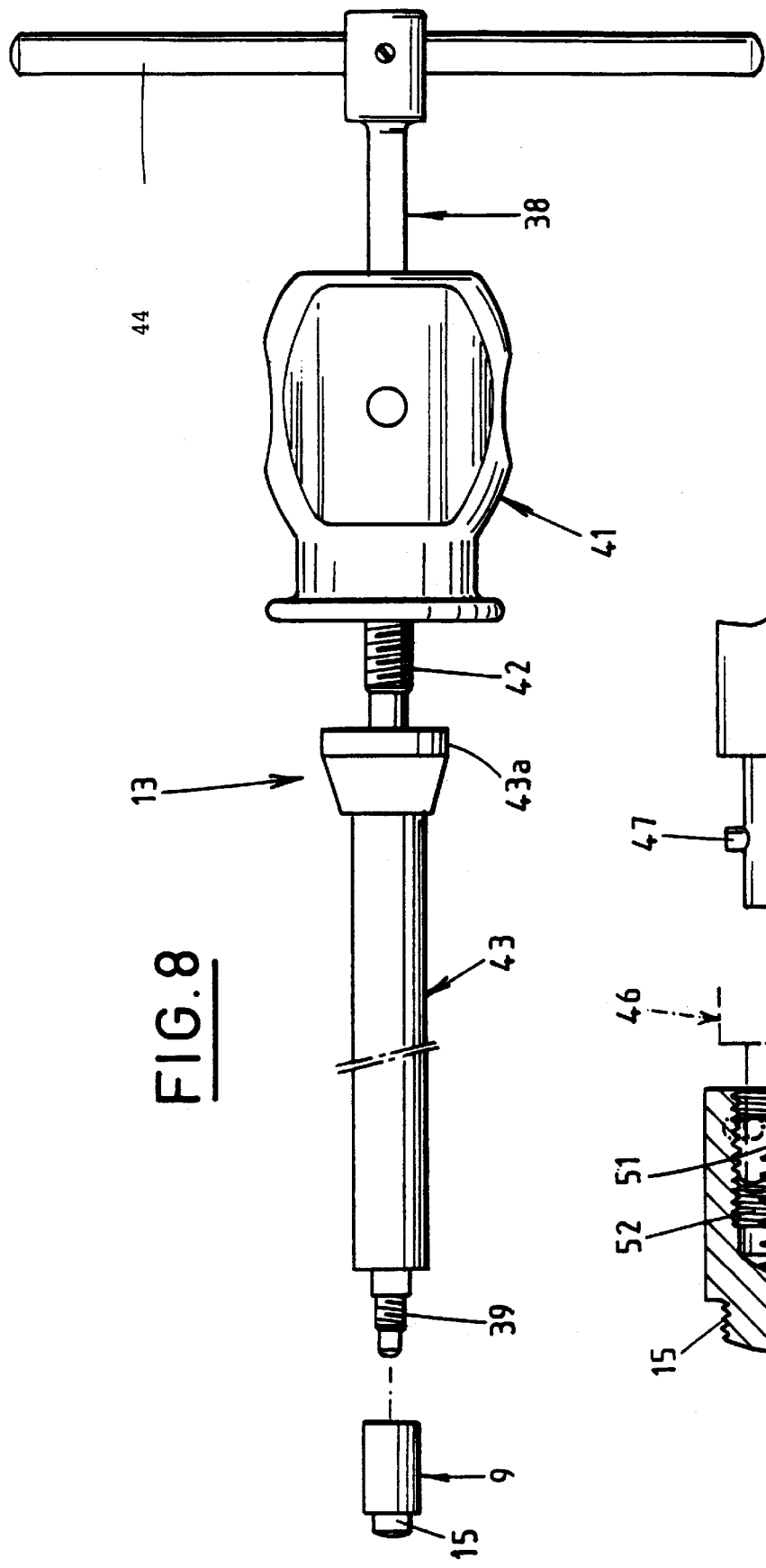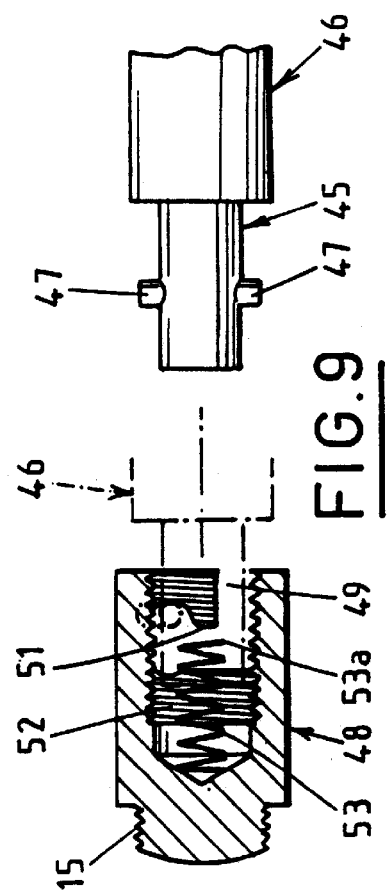

SET OF ANCILLARY EQUIPMENT FOR THE IMPLANTATION OF ACETABULAR CUPS OF HIP PROSTHESIS, AND PROSTHETIC ACETABULAR CUP ASSEMBLY READY TO BE IMPLANTED

FIELD OF THE INVENTION

The present invention relates to a set of ancillary equipment for the implantation of artificial acetabular cups of hip prostheses, of the type having a substantially hemispherical corolla, consisting of expandable petals which are provided with external barbs for anchoring in the bone. The invention also relates to an ancillary device which can be connected to and incorporated in the acetabular cups in order to permit their presentation and their implantation in the natural acetabulum of the patient.

BACKGROUND OF THE INVENTION

Acetabular cups of the corolla type are known which are formed by an assembly of expandable petals whose bases join in the area of the polar cap of the acetabular cup. These petals exhibit a certain amount of elasticity which allows them to be substantially drawn together in the radial direction. On their external surface, these petals are equipped with barbs ensuring anchoring in the osseous wall of the acetabulum when the surgeon effects a radial expansion of the petals by means of a suitable instrument.

However, the impaction and the osseous anchoring of these corolla-type acetabular cups present certain difficulties, which it is the aim of the invention to overcome by means of a suitable set of ancillary equipment.

SUMMARY OF THE INVENTION

According to the invention, the set of ancillary equipment for the implantation of acetabular cups of hip prostheses, of the corolla type, consisting of expandable petals provided with external barbs, comprises an obturator cover for closing the petals, under elastic radial stress, in a position in which they are drawn together, means for holding this obturator cover on the edges of the petals by connection with the bottom of the acetabular cup, an ancillary impaction device with which it is possible to impact the acetabular cup, freeing these petals by extraction of the obturator cover, a plate which expands the petals and which can be introduced into these petals after extraction of the obturator cover and release of the petals, and an ancillary device provided with means for driving the plate into the acetabular cup in order to permit the radial expansion of the petals after impaction, so as to ensure the anchoring of the acetabular cup by means of penetration of the anchoring barbs into the osseous wall of the acetabulum.

According to the invention, the acetabular cup of the corolla type mentioned above is produced, assembled and supplied by the manufacturer in the implantation state, that is to say including the obturator cover in its position holding the petals under elastic radial stress so that its total external equatorial diameter, upon its presentation in the natural acetabulum of the patient, is smaller than that of the natural acetabulum and so that the petals, after they have been released, can confer on the artificial acetabular cup the desired equatorial diameter, greater than the equatorial diameter in the position with the petals stressed.

According to other characteristics of the invention:

the means for holding and connecting the obturator cover to a polar zone, forming the bottom of the acetabular cup, comprise a tapped bushing provided with a threaded end finger which can be screwed axially into a corresponding tapped hole of the polar zone, and a plug including a head and a threaded end which can pass axially through the obturator cover in such a way as to be screwed into the bushing, while its head bears on the external face of the obturator cover; the thread at the end of the plug is screwed leftwards, while the ancillary device for impaction and extraction of the obturator cover has an end finger having a thread which is screwed rightwards into a complementary tapped hole of the plug; for this reason, the rightward screwing of the finger of the ancillary device into the plug effects the unscrewing of the latter and its extraction from the bushing, which permits extraction of the obturator cover.

Alternatively, the thread of the finger can be made to permit a leftward screwing, while the thread at the end of the plug is then made to permit a rightward screwing.

The ancillary device for impaction and extraction of the obturator cover includes a shaft mounted freely in translation inside a tubular grip, one end of the shaft is equipped with the said threaded finger designed to be screwed into the plug, while its opposite end bears a manoeuvring handle; the tubular grip includes, at one of its ends, at least one stud designed to be introduced into a complementary hole of the obturator cover, in order to prevent the rotation of the latter during the unscrewing of the plug held by the shaft.

The ancillary device for radial expansion of the petals of the acetabular cup comprises an axial rod equipped with an end designed to be able to be fixed to the bushing, itself integral with the polar zone of the acetabular cup, a tubular grip which is traversed axially by the rod and which can be screwed onto a threaded part of the latter, and a sleeve mounted freely in rotation and translation on the rod, between the tubular grip and the end cooperating with the bushing, in such a way that the screwing of the tubular grip exerts on the sleeve an axial thrust which is transmitted to the plate, which is driven into the petals and effects their radial expansion.

Such a set of ancillary devices considerably facilitates the task of the surgeon, allowing the latter, in a first stage, and by means of the first ancillary impaction device, to release the petals from the elastic retention pressure which they are subjected to by the obturator cover, in such a way that they assume their deployed free position in the acetabular wall. In a second stage, the surgeon uses the second ancillary device, and the associated plate introduced into the acetabular cup in the substantially equatorial position, in order to drive this plate into the acetabular cup and thereby effect the radial spreading of the petals and their anchoring, by means of the barbs, in the subchondral bone.

BRIEF DESCRIPTION OF THE DRAWINGS

Other features and advantages of the invention will become evident during the following description in which reference is made to the attached drawings which illustrate two embodiments of the invention by way of nonlimiting examples.

FIG. 8 is a longitudinal elevation view of the ancillary device for radial expansion of the acetabular cup, partially represented in FIG. 7.

FIG. 9 is a partial elevation view of a second embodiment of the ancillary device for radial expansion in FIG. 8, and a longitudinal cross-section of the associated bushing designed to be fixed in the bottom of the acetabular cup.

DETAILED DESCRIPTION OF THE INVENTION

Figure 1:
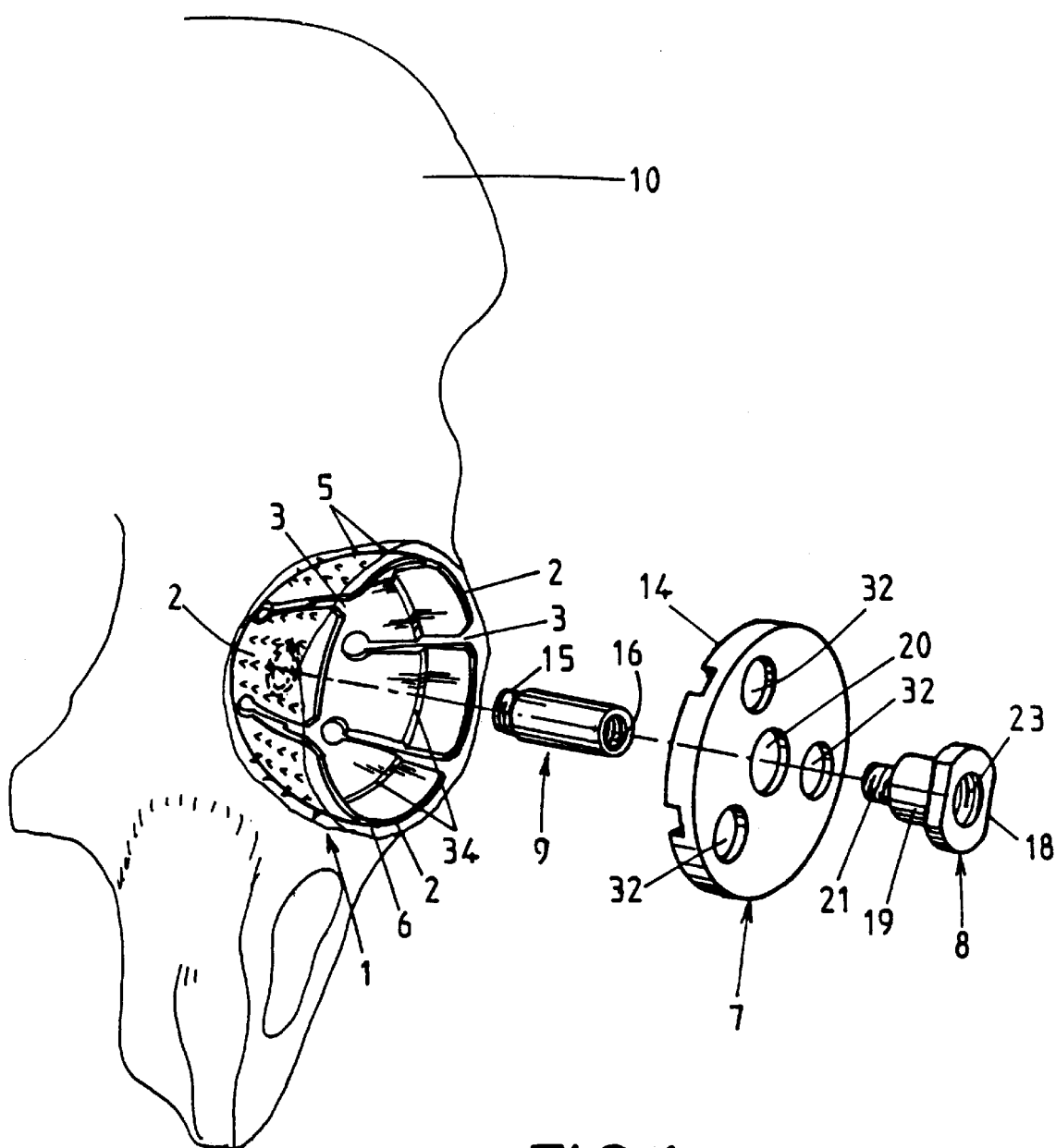
FIG. 1 is an exploded perspective view of an embodiment of the acetabular cup of a hip prosthesis, the obturator cover and the means for connecting the latter to the bottom of the acetabular cup, the latter being represented in place in an acetabular cavity of a hip.

The drawings show a substantially hemispherical acetabular cup 1 of the corolla type consisting of a series of expandable petals 2 which are separated by slots 3. The petals 2 join at their base in the area of the polar cap 4 of the acetabular cup 1 and are equipped on their external surface with an assembly of barbs 5 forming points for osseous anchoring in the wall of the acetabular cavity 6 of the iliac bone 10 (FIG. 1).

The acetabular cup 1 can be impacted into the acetabular cavity 6, and its petals anchored via the barbs or points 5 after radial expansion, by means of a set of ancillary equipment described hereinbelow.

This set. comprises an obturator cover 7 constituting a cover for closing the petals 2, members 8, 9 for holding the obturator cover 7 on the equatorial edges of the petals 2 and for connection with the bottom 4 of the acetabular cup 1, an ancillary impaction device 11 with which it is possible to impact the acetabular cup into the cavity 6; the set of ancillary equipment also includes a plate 12 which can be introduced into the acetabular cup 1 after extraction of the obturator cover 7, and a second ancillary device 13 which can cooperate with the plate 12 so as to effect the radial expansion of the petals 2 and, consequently, their anchoring in the acetabular wall via the points or barbs 5.

The obturator cover 7 and its holding members 8, 9 will be described first.

The petals 2 present a relative elasticity which allows them to be compressed radially when they are capped by the obturator cover 7, which, for this purpose, has a peripheral collar 14 (FIGS. 1, 2 and 4) for holding the petals 2 in the radially drawn-together and compressed position. To be able to perform this function, the circular cover 7 and its collar 14 have a diameter which is slightly smaller than that of the petals 2 in the free deployed state (FIGS. 1 and 2) : this difference in diameter appears clearly in FIG. 4, which partially shows the petals 2a in the free deployed position, and these same petals, in continuous lines, compressed and drawn together by introduction of their ends inside the collar 14.

The means for holding and connecting the obturator cover 7 to the polar zone 4, forming the bottom of the acetabular cup 1, comprise a tapped bushing 9 provided with a threaded end finger 15 and with a tapped blind hole 16. The finger 15 can be screwed axially into a corresponding tapped hole 17 formed axially in the polar zone 4. The device for holding the obturator cover 7 on the acetabular cup 1 also includes a plug 8 having a head 18, a body 19 and a threaded end 21. The body 19 and the end 21 can pass axially through the obturator cover 7, via a central hole 20 in the latter, in order to allow the end 21 to be screwed into the blind hole 16 after the finger 15 has been screwed into the hole 17 and after the obturator cover 7 has been put into place by virtue of the petals 2 being drawn together using means which are known per se.

Figure 6:
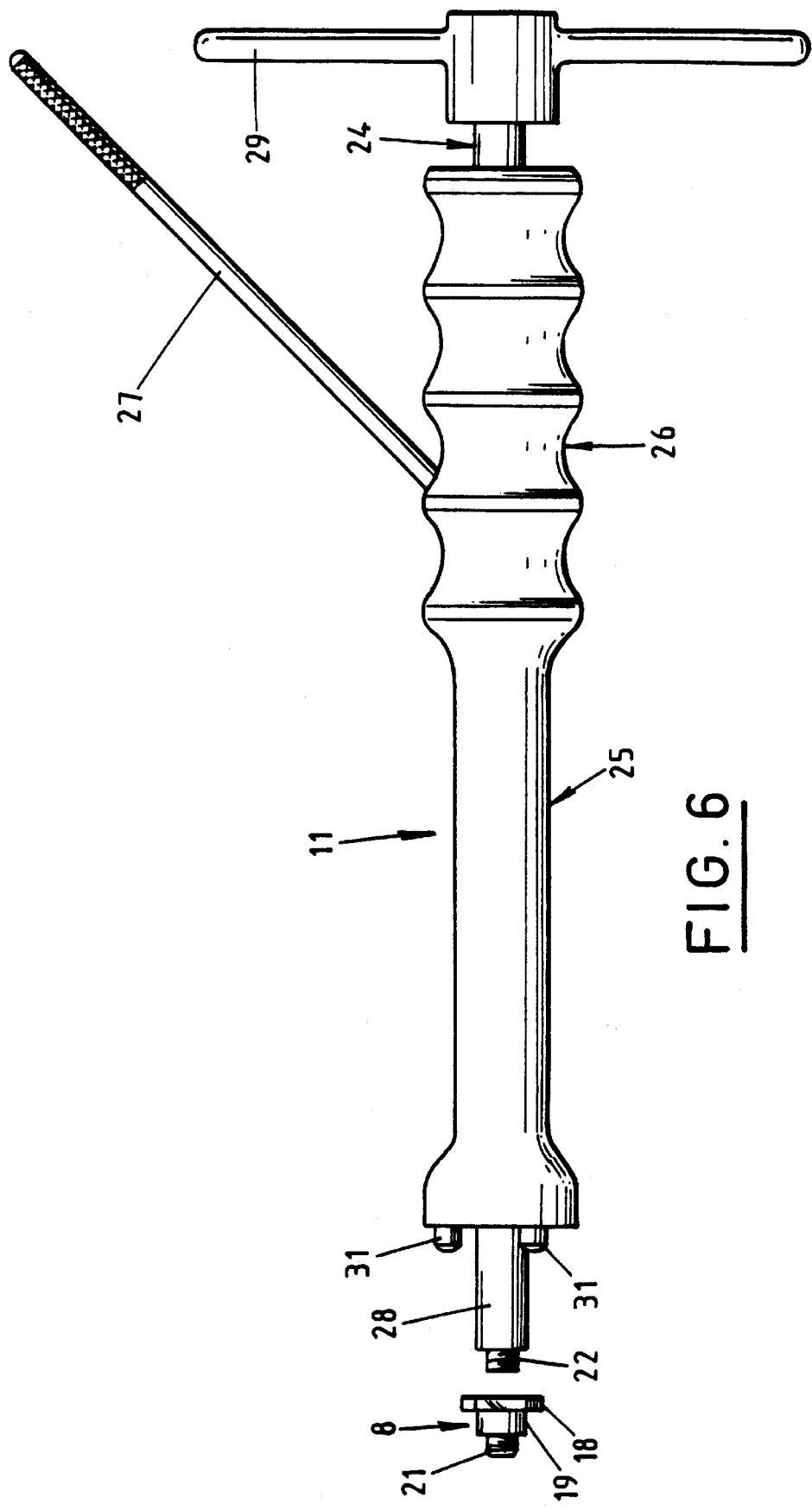
FIG. 6 is a longitudinal elevation view of an embodiment of the ancillary device for impaction of the acetabular cup in FIGS. 1 to 5.

The thread at the end 21 of the plug 8 is advantageously screwed leftwards, while the ancillary impaction device 11 has an end finger 22 (FIG. 6) with a thread which is screwed rightwards into a complementary tapped hole 23 in the plug 8. The thread at the end 15 of the bushing 9 is screwed rightwards. For this reason, the rightward screwing of the finger 22 of the ancillary impaction device 11 (which will be described in detail hereinafter) into the tapped hole 23 effects the unscrewing of the plug 8 relative to the bushing 9 and its extraction from the latter, and this permits the release and extraction of the obturator cover 7.

Alternatively, the thread at the end 22 of the ancillary device 11 could be threaded leftwards, and, conversely, the thread at the end 21 of the plug 8 could be threaded rightwards.

According to an alternative embodiment which is not represented, the bushing 9 is of the bayonet type and is designed to cooperate with an instrument whose one end is equipped with a corresponding stud, the introduction of the latter into the bayonet device of the bushing making it possible for the bushing to be unscrewed and removed.

The ancillary device 11 for impaction and extraction of the obturator cover 7 includes (FIG. 6) a shaft 24 mounted freely in translation inside a tubular grip 25, advantageously having a ribbed zone 26 making it easier for the surgeon to hold, as well as a lateral control lever 27. One end 28 of the shaft 24 is equipped with the threaded finger 22 designed to be screwed into the plug 8, while its opposite end bears a manoeuvring handles 29. The tubular grip 25 includes, at one of its ends, at least one stud 31, for example three studs distributed at uniform angles, and two of which can be seen in FIG. 6. These studs 31 are designed to be introduced into complementary holes 32 in the obturator cover 7 (FIG. 1), in order to prevent rotation of the latter during the unscrewing of the retention plug 8 via the shaft 24.

To carry out the impaction of the acetabular cup 1, the surgeon proceeds as follows.

Figures 4, 5:
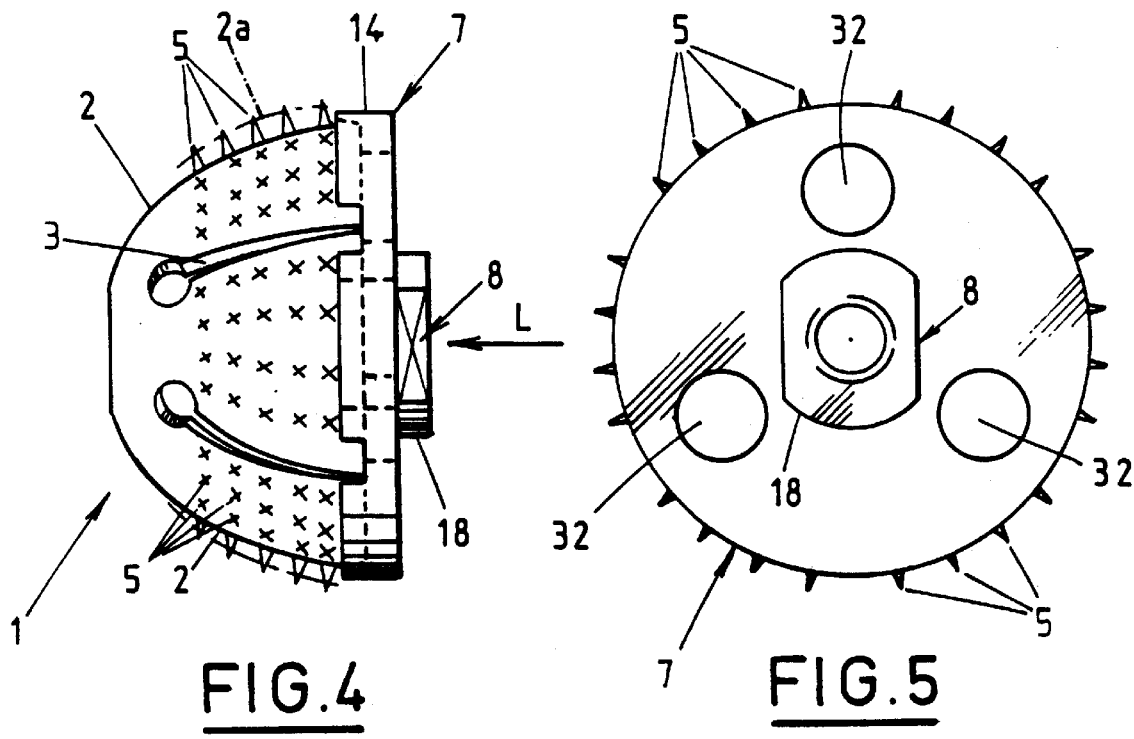
FIG. 4 is a side elevation view of the acetabular cup in FIGS. 1 to 3, equipped with the obturator cover for closure.
FIG. 5 is an elevation view in the direction of the arrow L in FIG. 4.

Initially, the assembly as represented in FIGS. 4 and 5, and consisting of the acetabular cup 1, the obturator cover 7, the plug 8 and the bushing 9, is manufactured and assembled and is thus supplied to the surgeon, who can have the rest of the ancillary equipment at hand.

The acetabular cup 1 is capped by the obturator cover 7 held in place on the petals 2, and compressing them radially, via the plug 8 and the bushing 9. The latter is screwed via its end 15 into the tapped hole 17, and the plug 8 is screwed through the hole 20 via its threaded finger 21 into the tapped hole 16 in the bushing 9. The surgeon introduces the threaded end 22 into the tapped hole 23 by screwing it rightwards, causing the studs 31 to pass into the holes 32. In this way, the obturator cover 7 is prevented from turning while the surgeon continues, with the aid of the manouevring handle 29, to screw the end 22 of the shaft 24 into the plug 8. The latter having been screwed leftwards, the continued rightward screwing of the shaft 24 unscrews the plug 8 from the bushing 9. Its extraction from the latter and from the obturator cover 7 releases the latter, so that by means of radial elastic resiliency, the petals 2 take up their impaction position 2a (FIG. 4) in which the barbs 5 partially penetrate into the osseous wall.

Figure 7:
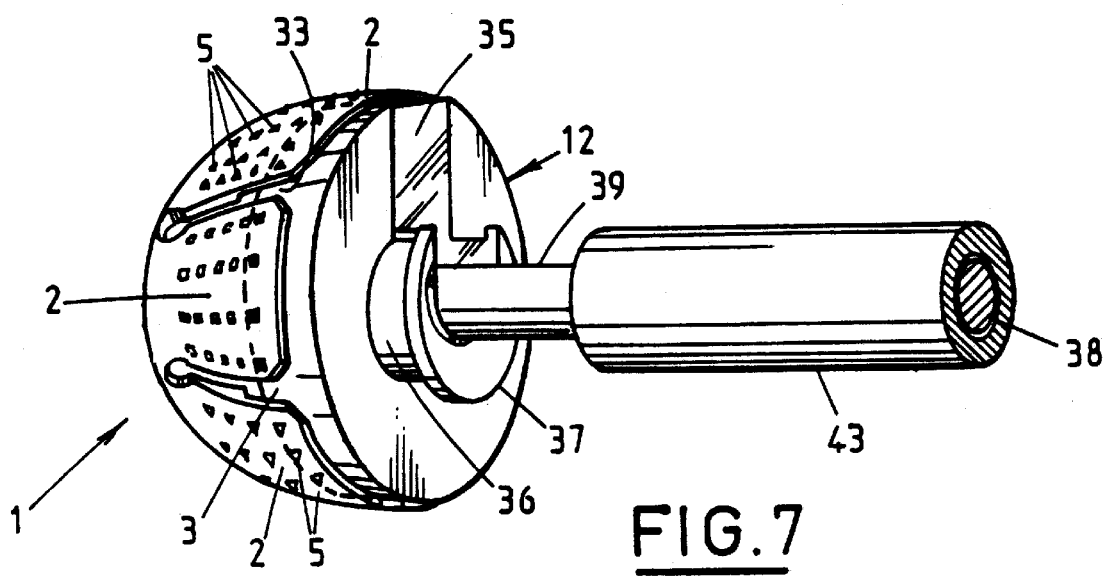
FIG. 7 is a perspective view of the acetabular cup equipped with a plate for radial expansion of its petals, and of a part of the corresponding ancillary device.

The radial expansion of the petals 2, to permit their definitive anchoring in the wall of the acetabular cavity 6, is effected by the surgeon by means of the ancillary device represented in FIGS. 7 to 9.

Figure 2:
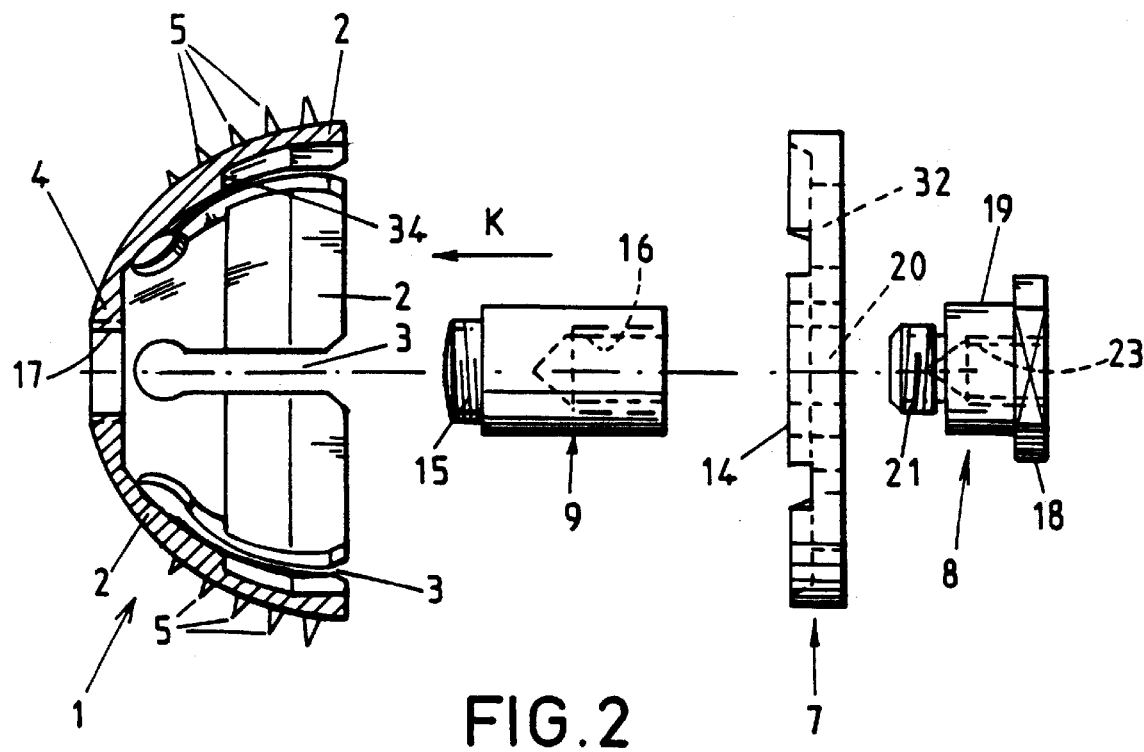
FIG. 2 is a side elevation view, in partial cross-section, corresponding to FIG. 1 and on a slightly enlarged scale.
Figure 3:
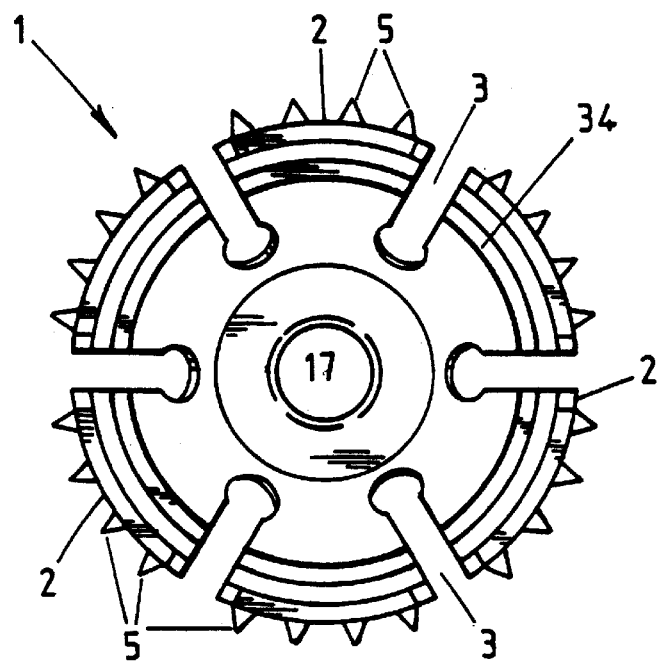
FIG. 3 is a plan view of the inside of the acetabular cup in the direction of the arrow K in FIG. 2.

This device includes the plate 12 which has a truncated surface 33 and is dimensioned in such a way as to be able to be introduced axially into the acetabular cup 1, exerting an increasing pressure on the petals 2 in order to effect their radial expansion. This expansion ends when the plate 12 comes into abutment on a shoulder 34 formed annularly on the inner wall of the petals 2 (FIGS. 1, 2, 3). The plate 12 additionally has Et radial slot 35 and is provided with a central collar 36 terminated by a circular flange 37 which is interrupted, as is the collar 36, by the slot 35. This arrangement allows the plate 12 to be manipulated by way of a gripping mechanism (not shown) which is known per se and is applied to the collar 36.

The ancillary device 13 for radial expansion of the petals 2 comprises (FIG. 8) an axial rod 38 equipped with an end 39 designed to be able to be fixed to the bushing 9, itself integral with the polar zone 4 of the acetabular cup 1. The ancillary device 13 also comprises a tubular grip 41, advantageously of an ergonomic design, traversed axially by the rod 38 and capable of being screwed onto the latter, which rod for this purpose has a threaded zone 42 engaging with a corresponding tapped bore in the tubular grip 41. The ancillary device 13 also includes a sleeve 43 mounted freely in rotation and in translation on the rod 38 between the tubular grip 41 and the end 39. The latter can be threaded (FIG. 8) and designed to be screwed into the bushing 9. The opposite end of the rod 38 is equipped with a transverse handle 44 allowing it to be manoeuvred in rotation.

The plate 12 and the ancillary expansion device 13 are used in the following way.

With the plate 12 introduced inside the petals 2 (FIG. 7) and with the bushing 9 screwed into the hole 17 of the polar cap 4, the surgeon introduces the threaded end 39 into the slot 35 in order to screw it into the bushing 9. He then slides the sleeve 43 until it comes into abutment against the flange 37. Finally, the surgeon screws the ergonomic grip 41 onto the threaded part 42 until this grip 41 comes into abutment on the end 43a of the sleeve 43 and exerts thereon an axial thrust which is transmitted by the sleeve 43 to the plate 12. The result is that the latter is driven into the petals 2 and effects their radial expansion, as well as the anchoring of the barbs 5 in the osseous wall of the cavity 6. The grip 41 is rotated clockwise until the truncated plate 12 has penetrated completely into the acetabular cup 1 and come into abutment on the stop shoulder 34. The powerful expansion of the petals 2 permits the anchoring of the barbs 5 in the subchondral bone.

Once the anchoring has been effected, the surgeon unscrews the ergonomic grip 41 anticlockwise, then pulls the plate 12 back with the aid of a gripping mechanism (not shown). The bushing 9 is also unscrewed.

According to a second embodiment (FIG. 9), the end 45 of the axial rod 46 includes at least one transverse stud 47, preferably two, and the bushing 48 has a bayonet arrangement with two longitudinal slots 49 and two corresponding notches 51 for retaining the studs 47. These bayonet elements are formed in the wall of a tapped hole 52, on the bottom of which an internal spring 53 can bear, one end 53a of which spring cooperates with the end part 45 in order to hold the studs 47 in the notches 51 of the bayonet system.

Thus, the tapped hole 52 can receive either an axial rod 38 with threaded end 39, or an axial rod 46 with an end 45 equipped with studs 47.

We claim:

1. Set of ancillary equipment for implanting an acetabular cup of a hip prosthesis, the cup having a substantially hemispherical corolla, consisting of a bottom polar zone, and expandable petals which are provided with external anchoring barbs, the set comprising:

an obturator cover for closing the petals, under elastic radial stress, in a position in which the petals are drawn together;

means for holding the obturator cover on edges of the petals by connection with the bottom polar zone of the acetabular cup;

an ancillary impaction device for impacting the acetabular cup, releasing the petals by extraction of the obturator cover;

a plate which expands the petals and which can be introduced into the petals after extraction of the obturator and release of the petals; and an ancillary expansion device provided with means for driving the plate into the acetabular cup in order to permit radial expansion of the petals after impaction, so as to ensure anchoring of the acetabular cup by penetration of the anchoring barbs into an osseous wall of an acetabulum.

2. The set according to claim 1, wherein the obturator cover includes a peripheral collar for holding the petals, said collar having a diameter which is slightly smaller than that of the petals when released.

3. The set according to claim 2, wherein the means for holding the obturator cover to the polar zone comprise a tapped bushing having a threaded end finger adapted to be screwed axially into a corresponding tapped hole of the polar zone, and a plug including a head and a threaded end structured and arranged to pass axially through the obturator cover and be screwed into the bushing, while the head bears on an external face of the obturator cover, said threaded end adapted to be screwed in a first direction, while the ancillary impaction device includes an end finger having a thread adapted to be screwed in a second opposite direction into a complementary tapped hole of the plug, such that the screwing of the finger of the ancillary impaction device into the plug effects the unscrewing and extraction of the plug from the bushing, thereby permitting extraction of the obturator cover.

4. The set according to claim 3, wherein the bushing is a bayonet device which is designed to cooperate with an instrument having an end equipped with a corresponding stud, whereby introduction of the instrument into the bayonet device makes it possible for the bushing to be unscrewed and removed.

5. The set according to claim 4, wherein the ancillary impaction device includes a shaft mounted freely in translation inside a tubular grip, one end of the shaft being equipped with said threaded finger designed to be screwed into the plug, while its, opposite end bears a maneuvering handle, said tubular grip including at one of its ends at least one stud designed to be introduced into a complementary hole in the obturator cover, in order to prevent rotation of the obturator cover during unscrewing of the plug via the shaft.

6. The set according to claim 3, wherein the plate is truncated and is adapted to be driven into the corolla of the acetabular cup as far as an abutment shoulder formed annularly on an inner wall of the petals.

7. The set according to claim 6, wherein the plate has a radial slot and a central collar adapted to be gripped by a gripping mechanism, and terminated by a small retention flange.

8. The set according to claim 6, wherein the ancillary expansion device comprises an axial rod having an end adapted to be fixed to the bushing, a tubular grip which is traversed axially by the rod and capable of being screwed onto a threaded part of the rod, and a sleeve mounted freely in rotation and translation on the rod, between the tubular grip and the end cooperating with the bushing, such that screwing of the tubular grip exerts on the sleeve an axial thrust which is transmitted to the plate.

9. The set according to claim 8, wherein the end of the axial rod is threaded and adapted to be screwed into the bushing.

10. The set according to claim 8, wherein the end of the axial rod includes at least one transverse stud and the bushing has a bayonet arrangement structured and arranged to receive the stud, and an internal spring bearing on the bottom of a tapped hole of the bushing in order to hold the end of the rod in the bayonet arrangement, whereby the tapped hole may receive either a threaded end or an end equipped with at least one stud.

\* \* \* \* \*